(12) United States Patent
Roskos et al.

(10) Patent No.: US 6,224,883 B1
(45) Date of Patent: May 1, 2001

(54) PROCESS AND COMPOSITION FOR THERAPEUTIC CISPLATIN (CDDP)

(75) Inventors: Kathleen V. Roskos, Los Altos Hills; Richard E. Jones, Palo Alto; Richard Maskiewicz, Sunnyvale, all of CA (US)

(73) Assignee: Matrix Pharmaceutical, Inc., Fremont, CA (US)

( * ) Notice: Subject to any disclaimer, the term of this patent is extended or adjusted under 35 U.S.C. 154(b) by 0 days.

(21) Appl. No.: 09/013,568

(22) Filed: Jan. 26, 1998

Related U.S. Application Data

(62) Division of application No. 08/550,086, filed on Oct. 30, 1995, now Pat. No. 6,077,545.

(51) Int. Cl.[7] .............................. A61K 31/28; A61K 9/10
(52) U.S. Cl. ............................................ 424/400; 514/492
(58) Field of Search .............................. 424/400; 514/492

(56) References Cited

U.S. PATENT DOCUMENTS

| Re. 33,375 | * | 10/1990 | Luck et al. ................................ 514/2 |
| 4,619,913 | * | 10/1986 | Luck et al. ................................ 514/2 |
| 4,863,902 | | 9/1989 | Amagase et al. ...................... 514/12 |
| 5,019,394 | | 5/1991 | Hamaguchi et al. ................. 424/423 |
| 5,100,877 | | 3/1992 | Mori et al. .............................. 514/54 |
| 5,214,174 | * | 5/1993 | Mayamoto et al. .................. 556/137 |
| 5,750,146 | * | 5/1998 | Jones et al. ........................... 424/484 |

FOREIGN PATENT DOCUMENTS

91/14455  10/1991  (WO) .

OTHER PUBLICATIONS

Araki et al Gastroint. Radiology 14:4648 1989.*
Yodono et al Cancer Chemother. Pharmacol. 42–44.*
Natsume et al Drug Delivery Systems 1991 6(3) 213–19.*
PDR(1999) p. 793.*
Araki et al., "Newly Developed Transarterial Chemoembolization Material: CDDP–Lipiodol Suspension," *Gastrointest. Radiol.*, 14:46–48 (1989).

Nagase et al., "Effects of Intralesional Versus lp Administration of Cisplatin on Squamous Cell Carcinoma of Mice," *Cancer Treatment Reports*, 71:825–829 (1987).
Theon et al, "Intratumoral Chemotherapy with Cisplatin in Oily Emulsion in Horses,"*JAVMA*, 202:261–267 (1993).
Landrito et al., "Effects of Intralesional Injection of Cisplatin Dissolved in Urografin and Lipiodol on Ehrlich Ascites Tumor and Normal Tissues of CD–1 Mice," *Cancer Chemother. Pharmacol.*, 34:323–330(1994).
Sternlicht et al., "Renal Cisplatin Chemoembolization with Angiostat, Gelfoam, and Ethiodol in the Rabbit: Renal Platinum Distributions," *Radiology*, 170:1073–1075 (1989).
Yodono et al., "Combination Chemoembolization Therapy for Hepatocellular Carcinoma: Mainly, Using Cisplatin (CDDP)," *Cancer Chemother. Pharmacol.*, 23:42–44 (1989).
Verrijk et al., "Reduction of Systemic Exposure and Toxicity of Cisplatin by Encapsulation in Polylactide–co–glycolide," *Cancer Research*, 52:6653–6656 (1992).
Ichida et al, "Treatment of Hepatocellular Carcinoma with a CDDP–Eirubicin–Lipiodol Suspension: A Pilot Clinico–Pharmacological Study," *Cancer Chemother. Pharmacol.*31:51–54 (1992).
Wagner and Engelmann, "Studies of the Absorption Behavior of Cisplatin After Bladder Infusion in an Animal Model," *Fortschr. Atomspektrom. Spurenanal.*, 2:139–149 (1986).
Natsume et al., "Investigation on Utility of Viscous Ethyl Oleate Containing Cis–Diamminedichloroplatinum(II) in Tumor–Bearing Animals," *Drug Delivery Syst.*, 6(3):213–219 (1991).

* cited by examiner

*Primary Examiner*—Peter F. Kulkosky
(74) *Attorney, Agent, or Firm*—Flehr Hohbach Test Albritton & Herbert LLP

(57) ABSTRACT

An improved diluent for the preparation of cisplatin suspensions from a lyophilized powder is provided. The diluent contains a pharmaceutically acceptable nonionic surfactant, which improves the accuracy and homogeneity of the therapeutic formulation. The suspension may be used directly, or may be used in preparing gel formulations for direct injection into a neoplastic lesion or surrounding tissue.

15 Claims, No Drawings

PROCESS AND COMPOSITION FOR THERAPEUTIC CISPLATIN (CDDP)

This is a divisional of application Ser. No. 08/550,086 filed Oct. 30, 1995, now U.S. Pat. No. 6,077,545.

Technical Field

The field of this invention is preparation of injectable cisplatin (cis-diamminedichloroplatinum, CDDP) compositions.

BACKGROUND

Cisplatin (cis-diamminedichloroplatinum, CDDP) is an antineoplastic drug that has been used in cancer chemotherapy for a number of years. It is typically administered intravenously as an aqueous solution, either as a bolus injection or via infusion over a number of hours. It has been marketed both as a lyophilized powder for reconstitution into an aqueous solution, or as a ready-to-use aqueous solution. Intravenous delivery typically requires an aqueous solution, or, in some cases, a liquid emulsion or liposome system, wherein solid particulates which may occlude vessels and capillaries are absent. The concentration of CDDP in such intravenously injectable solutions is limited by its solubility in water, on the order of 1 mg/ml.

Cisplatin has also been administered in various forms for locoregional delivery, such as administration to the liver via infusion into the hepatic artery. In these cases, the drug can be administered in solution or emulsion forms above (for example, see Campbell et al. (1983) *J. Clin. Oncol.* 1:755–762). It can also be administered along with materials intended to bring about embolization in the target organ, thus blocking blood flow through that organ, inhibiting clearance of the CDDP away from the target organ. The cisplatin in these cases is typically in solution in water, but also may be combined with other nonaqueous materials such as iodized oil (Lipiodol; for example. see Araki et al. (1989) *Gastrointest. Radiol.* 14:46–48 or Feun et al. (1994) *Am. J. Clin. Oncol.* 17:405–410) or polyvinyl alcohol particles (Mavligit et al. (1993) *Cancer* 72:375–380). Unfortunately, this procedure is often associated with significant toxicity and morbidity to the patient, due to the blockage of blood flow to normal parts of the liver.

Another approach to the delivery of cisplatin to solid tumors has involved direct intralesional injection. Simple aqueous solutions of cisplatin have been reported for this use, as have simple oil/water emulsions and aqueous collagen gels. The dose of cisplatin achievable with these systems is, as above, limited by the solubility of cisplatin in water (approximately 1.2 mg/ml) and the volume of solution that can be successfully administered to the target tissue. Higher doses can produce an enhanced therapeutic gain, but require the use of suspensions of drug rather than solutions.

For injection directly into tumor tissue or tissue other than the bloodstream, higher concentrations of drug are of significant benefit and desirability, to provide higher drug loads and improved drug efficacy at or near the site of injection. Because the administration is not into the bloodstream, the presence of particulates is not proscribed. Reconstitution of cisplatin powder to a suspension rather than a solution, then, becomes of great interest.

U.S. Pat. No. Re 33,375, provides an example where a vial of lyophilized CDDP is first reconstituted with water for injection into a concentrated suspension of drug. A small amount of epinephrine solution is optionally added to this cisplatin suspension, then a portion of the suspension is withdrawn from the vial (via syringe and needle) and mixed with a collagen gel to yield a final gel preparation (containing a suspension of cisplatin) ready for administration.

Another example is provided in Theon et al. (1993) *J. Am. Vet. Med. Assoc.* 202:261–267, in which lyophilized CDDP is reconstituted with water to form a concentrated suspension of drug, then mixed with sesame oil to produce a water-in-oil emulsion that is subsequently injected directly into tumors in horses.

Reconstitution of lyophilized CDDP to a suspension in this fashion with water alone results in relatively large particles of drug which settle rapidly, resulting in inhomogeneous suspensions. This is turn results in CDDP preparations having CDDP content below the theoretical target value, and exhibiting considerable variability between nominally identical syringes of final gel. Methods which reduce the variability and improve recovery during suspension reconstitution are therefore of interest.

Relevant Literature

The use of collagen-based gels for delivery of chemotherapeutic drugs is described in U.S. Pat. No. Re. 33,375.

A non-aqueous suspension of CDDP in lipiodol® for transarterial chemoembolism is described in Araki et al. (1989) *Gastrointest. Radiol.* 14:46–48. Landrito et al. (1994) *Cancer Chem. and Pharm.* 34:323–330 teaches the effects of intralesional injection of cisplatin dissolved in urografin and lipiodol®. The treatment of hepatocellular carcinoma with a CDDP-epirubicin-lipiodol® suspension is described in Ichida et al. (1992) *Cancer Chem. Pharm.* 31:S51–S54.

The effects of intralesional vs. ip administration of cisplatin is described in Nagase et al. (1987) *Cancer Treatment Reports* 71:825–829. Theon et al. (1993) *JAVMA* 202:261–267 describes intratumoral chemotherapy with an oily emulsion of cisplatin.

Sternlicht et al. (1989) *Radiology* 170:1073–1075 investigates renal cisplatin chemoembolization with angiostat, gelfoam, and ethiodol. A combination chemoembolization therapy for hepatocellular carinoma is described in Yodono et al. (1989) *Cancer Chem. and Pharm.* 23:S42–S44. The reduction of systemic exposure and toxicity of cisplatin by encapsulation in poly-lactide-co-glycolide is taught by Verrijk et al. (1992) *Cancer Res.* 52:6653–6656.

SUMMARY OF THE INVENTION

Inclusion of a pharmaceutically-acceptable nonionic surfactant in an aqueous reconstitution vehicle for reconstitution of CDDP powder provides a small-particle suspension. Sampling of this suspension and formulation for injection is accomplished more accurately and with greater recovery and less variability than if water for injection is used alone.

DESCRIPTION OF THE SPECIFIC EMBODIMENTS

An improved diluent for the preparation of CDDP suspensions from a lyophilized powder is provided. The diluent is useful where a suspension is preferred over a solution of the drug, particularly in gel formulations for direct injection into a neoplastic lesion or surrounding tissue. Inclusion of a pharmaceutically acceptable nonionic surfactant improves the efficacy and homogeneity of the therapeutic formulation.

It is desirable to have CDDP in a uniform, stable suspension for preparation of injectable formulations, because one can then achieve a higher concentration of drug in the injectable formulation and thereby deliver a higher quantity of drug while limiting the injection volume. The solubility of CDDP in water is about 1 mg/ml. The concentration of CDDP in the subject suspensions will usually be greater than about 2 mg/ml, more usually greater than about 3.5 mg/ml, and usually less than about 20 mg/ml, more usually less than about 8 mg/ml. A suspension of CDDP also allows release of the drug at the site of injection over a period of time. The drug becomes bioactive as the particles go into solution.

Lyophilized CDDP is intended for reconstitution into a solution rather than a suspension. The standard vehicle for such solution reconstitution is Water for Injection (WFI). When this vehicle is used to reconstitute lyophilized CDDP into a suspension, however, large agglomerates of CDDP crystals or particles are produced, rather than a fine dispersion of individual particles or crystals. Such agglomerates settle rapidly, resulting in inhomogeneous material. Recovery of the CDDP from vials is therefore incomplete and variable, depending on how much of the total suspended dose has settled into portions of the vial inaccessible to the needle used for suspension removal.

A suspension of small particles is preferred to large particles. Small particles are more homogeneously distributed throughout the therapeutic formulation, providing a finished suspension with more accurate and precise drug concentration. Small particles settle less rapidly and are more easily maintained as a homogenous dispersion. This allows more accurate and precise transfers of drug dose during preparation and administration. The larger surface to volume ratio of small particles also provides a higher solubilization rate, thereby increasing the rate at which the drug becomes biologically active.

An aqueous suspension of CDDP is particularly useful for intralesional injection. Additional therapeutic benefits are obtained in the treatment of solid tumors, or adjacent tissues which may contain tumor cells, by employing a substantially uniform dispersion of CDDP in a physiologically acceptable gel matrix, e.g. collagen, fibrinogen or derivatives and combinations thereof, dispersed in a physiologically acceptable aqueous medium. The gel is injected into the neoplastic lesion, e.g. tumor, or lesion area, e.g. surrounding tissues, or in those situations where the tumor mass has been removed, tissue adjacent to the previously removed tumor and/or into the cavity remaining after removal of the tumor. The gel is flowable for injection, but provides for stable placement and retention of drug once injected into the tissue. After injection, the drug is released into the immediate environment, while circulating blood levels of the drug remain low. An enhanced therapeutic gain is achieved by having a higher concentration of CDDP at the site of malignant cells as compared to susceptible normal cells. In some cases it may also be desirable to inject aqueous CDDP suspension or gel intramuscularly or intra-peritoneally.

The use of a pharmaceutically acceptable nonionic surfactant to aid in the resuspension of lyophilized CDDP provides a uniform, small particle suspension. Suitable nonionic surfactants are polysorbates, sorbitan esters, poloxamers, polyethoxylated fatty alcohols, e.g. Brij®, polyethoxylated fatty acid esters, e.g. Myrj®, and the like. Of particular interest are polysorbates, e.g. polysorbate 20 and polysorbate 80. Polysorbate helps to disperse the CDDP crystal clusters which would otherwise remain agglomerated as large, rapidly sinking particles. The surfactant will usually be present in an aqueous diluent at a concentration greater than from about 0.01% weight/volume, usually greater than about 0.05%, preferably at about 0.1%, and usually at a concentration less than 0.75%, more usually less than 0.25%.

The final therapeutic formulation will optionally include epinephrine, which has been shown to increase the local retention of an injected dose, and therefore the antineoplastic efficacy. The inclusion of epinephrine into the diluent is of benefit in simplifying the formulation preparation. Epinephrine will usually be present in the diluent at a concentration greater than about 0.01 mg/ml, more usually greater than about 0.05 mg/ml, and usually at a concentration less than about 0.5 mg/ml, more usually less than about 0.25 mg/ml.

If epinephrine is included, it is desirable to formulate the composition of diluent to maximize epinephrine stability. The inclusion in the diluent of EDTA, usually at a concentration greater than about 0.01 mg/ml and less than about 0.5 mg/ml, more usually at about 0.1 mg/ml, and sodium metabisulfite, usually at a concentration greater than about 0.02 mg/ml and less than about 0.5 mg/ml, more usually at about 0.2 mg/ml, provides a stable solution of epinephrine. Optionally, carboxymethylcellulose sodium may also be included to enhance suspension stability, usually at a concentration greater than from about 0.01% weight/volume, usually greater than about 0.05%, and usually at a concentration less than 0.5%, more usually less than 0.25%.

The diluent will be buffered with a pharmaceutically acceptable buffer system to achieve an acidic pH, usually greater than about 2 and less than about 5, more usually about pH 4. Buffer pairs, particularly carboxylic acids and their salts, such as acetic acid-sodium acetate, succinic acid-sodium succinate and citric acid-sodium citrate may be used. The combined concentration of buffer pair in the diluent will usually be greater than about 5 mM and less than about 50 mM, more usually about 10 mM.

The lyophilized CDDP is reconstituted with the diluent to form a stable suspension. If the CDDP suspension is to be formulated into a gel, it is then mixed with a gelling agent, e.g. collagen, to form the amorphous gel, as provided for in U.S. Pat. No. Re. 33,375. The collagen employed may be natural collagen or may be modified, such as tropocollagen, atropocollagen, or the like. The collagen may be non-immunogenic, immunogenic, or slightly immunogenic. Various methods for preparing collagen or derivatives thereof in purified form for administration to a mammalian host are found in the literature. Purification will normally involve dispersion or precipitation from various media. Conveniently, bovine or porcine collagen is readily available. The collagen will usually be in an aqueous gel form at a concentration greater than about 1%, more usually greater than about 2%, and usually less than about 8% weight/volume.

The subject compositions will be administered to a tumor to provide a cytotoxic amount of drug at the tumor site. In view of the wide diversity of tumors, nature of tumors, effective concentrations of drug, relative, mobility and the like, a definitive range cannot be specified. In each tumor, experience will provide an optimum level. One or more administrations may be employed, depending on the lifetime of the drug at the tumor site and the response of the tumor to the drug. Administration may be by syringe, catheter or other convenient means for allowing for introduction of a flowable composition into the tumor. Administration may be every three days, weekly, or less frequent, such as biweekly or at monthly intervals. The presence of surfactant does not adversely affect cytotoxic activity.

The subject methods find particular advantage with tumors or lesions which are clinically relevant. The compositions provide therapeutic gains with tumors greater than 100 mm$^3$, more particularly, greater than 150 mm$^3$ in volume. Illustrative tumors include carcinomas, sarcomas and melanomas, such as basal cell carcinoma, squamous cell carcinoma, melanoma, soft tissue sarcoma, solar keratoses, Kaposi's sarcoma, cutaneous malignant lymphoma, Bowen's disease, Wilm's tumor, hepatomas, head-and-neck cancers, testicular and ovarian cancers, bladder cancer, colorectal cancer, brain tumors, mycosis fungoides, Hodgkin's lymphoma, polycythemia vera, lymphomas, oat cell sarcoma, etc.

In order to address the needs of a clinical laboratory, a kit may be provided having the reagents and apparatus necessary to perform the subject invention. Such a kit may include vials of lyophilized CDDP, diluent for CDDP resuspension, collagen gel, and syringes for mixing and dosing. Epinephrine may be included in the diluent.

The following examples are offered by way of illustration and not by way of limitation.

EXPERIMENTAL

Example I

Preparation of CDDP Suspensions with WFI or Custom Diluent

Two custom diluents, differing only in the presence of carboxymethylcellulose sodium were formulated. Compositions are provided below.

|  | Custom Diluent | |
| --- | --- | --- |
|  | Diluent A per ml | Diluent B per ml |
| epinephrine, USP | 0.160 mg* | 0.160 mg |
| polysorbate 80, NF | 1.00 mg | 1.00 mg |
| edetate disodium (dihydrate), USP | 0.10 mg | 0.10 mg |
| carboxymethylcellulose sodium, USP | — | 0.50 mg |
| sodium metabisulfite, NF | 0.20 mg | 0.20 mg |
| glacial acetic acid, USP | 0.49 mg | 0.49 mg |
| sodium acetate, anhydrous, USP | 0.15 mg | 0.15 mg |
| WFI, USP | qs to 1.00 ml | qs to 1.00 ml | with HCl and/or NaOH, if necessary, to adjust pH to 4.0
*includes 5% overage

Preparation of Diluent

Diluent was prepared at a nominal epinephrine concentrations of 0.152 mg/ml (plus 5% overage), by dissolving all the above mentioned ingredients, with the exception of epinephrine, in an appropriate volume of water for injection. The solution was sparged with nitrogen for 30 minutes, the required amount of epinephrine was added, and the mixture was stirred under a nitrogen blanket until the epinephrine dissolved. pH was adjusted if necessary, and additional WFI was added to achieve the final desired volume. The solution was sparged with nitrogen for an additional 30 minutes, and then sterile filtered through a 0.22 micron filter. Filtered solution was filled into 5 ml vials, the vial headspace was flushed with nitrogen, and the vials were stoppered and crimped.

Other materials used in this study were as follows. Cisplatin for Injection, USP (Platinol®, 10 mg vial) was the commercial product manufactured by Bristol Laboratories. Alternatively, lyophilized CDDP manufactured by Faulding (David Bull Laboratories, Australia) was used. Aqueous collagen gel, 6.5% was obtained from Collagen Corporation (Palo Alto, Calif.), 0.3 ml nominal fill in 1 ml plastic syringes. The gel is comprised of a highly purified, telopeptide-free bovine Type I collagen, 6.5% (w/w); sodium phosphates, 0.100M; sodium chloride, 0.045M; and has a nominal pH of 7.2. Epinephrine solution (1 mg/ml) was purchased (Adrenalin® Chloride Solution, Parke-Davis), 30 ml vial. Polysorbate 80 was obtained from PPG Industries. Carboxymethylcellulose sodium (NaCMC) was obtained from Aqualon. 0.9% Sodium Chloride Injection, USP (10 ml vial) ("saline") was manufactured by Abbott Laboratories. Sterile Water for Injection, USP (10 ml vial) ("WFI") was manufactured by Abbott Laboratories.

Reconstitution of Lyophilized CDDP

Vials containing either 10 mg or 25 mg of lyophilized CDDP were reconstituted by adding either 1.6 ml or 4.0 ml of diluent, respectively, to yield a suspension of CDDP. Gels containing CDDP were prepared with final volumes of 2.0 ml or 5.0 ml. The "2 ml" CDDP/epinephrine gel was prepared by withdrawing 1.4 ml of CDDP suspension from a 10 mg vial into a syringe, and mixing with 0.6 ml of 6.5% collagen gel (also in a syringe) via multiple intersyringe transfers. The "5 ml" CDDP/epinephrine gel was prepared by withdrawing 3.5 ml of CDDP suspension from a 25 mg vial into a syringe, and mixing with 1.5 ml of collagen gel (also in a syringe) via multiple intersyringe transfers. The final gel mixture was then transferred to one of the syringes for use in dosing. Both final gels contained 4.0 mg/ml CDDP and 0.1 mg/ml of epinephrine, in a 2% collagen matrix, and were ready for use.

A similar procedure was employed for the preparation of CDDP-containing gels, using WFI instead of the custom diluent to prepare the initial CDDP suspension. In this case 1.2 ml of WFI was added to a 10 mg vial of CDDP, followed by a 0.2 ml volume of commercial injectable epinephrine solution (1.0 mg/ml). The resultant suspension was further processed, as above.

Analysis of Gels for CDDP Concentration

Aliquots of final gels prepared above were dissolved by treatment with aqueous hydrochloric acid, and were subsequently diluted into a methanol: water mobile phase containing sodium chloride. Samples were then analyzed for CDDP content by a strong anion exchange HPLC method. Aliquots of final gel were obtained from multiple individually-prepared syringes of CDDP/epi gel. In addition, aliquots of gel from different regions of a given syringe were obtained and analyzed.

CDDP contents measured for individual syringes of final gel prepared using either of the custom diluents or WFI are described in Table 1. The data shows that a higher concentration of CDDP is found when custom diluent is used for reconstitution, and that subpotent CDDP concentrations are found in gels prepared from CDDP suspensions prepared with water alone.

A consistent reduction in intersyringe variability is also apparent for CDDP gels prepared using custom diluent. Comparing CDDP contents in several sets of syringes of final gel (each set representing data from 3 to 12 syringes), the relative standard deviation (RSD) for gels prepared using WFI ranged from 2.9–8.6% while gel sample sets prepared using custom diluent exhibited an RSD ranging from 1.2–4.6%.

An increase in CDDP content and dose reproducibility for individual syringes of final gel can also be achieved using a custom diluent containing carboxymethylcellulose sodium (NaCMC) in addition to polysorbate 80. Data in Table 1 for custom diluent additionally containing 0.05% NaCMC shows that the concentration of CDDP in syringes of final gel increased relative to samples prepared using WFI, and that the RSD's for sets of gel samples (syringes) prepared using NaCMC containing custom diluent were smaller than those for sample sets of final gel derived from cisplatin suspensions in WFI.

TABLE 1

Effect of Various Diluents on CDDP Drug Content and Intersyringe Dose Reproducibility in CDDP Gel Implants

| diluent | CDDP Content (mg/ml) | RSD (relative standard deviation) | n |
|---|---|---|---|
| WFI | 3.52 ± 0.21 | 6.0% | 12 |
| WFI | 3.78 ± 0.11 | 2.9% | 3 |
| WFI | 3.64 ± 0.31 | 8.6% | 3 |
| Diluent A | 4.43 ± 0.09 | 2.0% | 3 |
| Diluent A | 4.31 ± 0.20 | 4.6% | 3 |
| Diluent A | 4.14 ± 0.16 | 3.8% | 3 |
| Diluent A | 4.20 ± 0.09 | 2.1% | 3 |
| Diluent A | 3.94 ± 0.05 | 1.2% | 3 |
| Diluent B | 4.20 ± 0.14 | 3.3% | 9 |
| Diluent B | 4.27 ± 0.16 | 3.7% | 11 |

The data shown in Table 2 demonstrates that use of custom diluent results in increased recovery of cisplatin from lyophilized vials for all formulations, and in improved dose reproducibility. Measured CDDP content in CDDP gels prepared using vials of Platinol® reconstituted with WFI averaged 3.54±0.28 mg/ml of the final gel, only 80% of the target value. Reconstitution of vials of Platinol with custom diluent resulted in a final product containing 3.94±0.005 mg/ml CDDP, increasing the recovery to 89% of the target value. Reconstitution of 10-mg and 25-mg Faulding vials of CDDP with custom diluent resulted in final concentrations at 94–96% of the target value. As well as improved CDDP content, the variability of CDDP dose between syringes was decreased upon substitution of custom diluent for WFI. As shown in Table 2, variability of CDDP dose between individual syringes decreased from an RSD of 7.9% to RSDs of about 1.3% to 3.8% upon substitution of custom diluent for WFI for reconstitution of vials.

TABLE 2

| Formulation | Sample (Syringe) # | CDDP Content (mg/ml) |
|---|---|---|
| WFI/10 mg Platinol ® | 1 | 3.35 |
| " | 2 | 3.27 |
| " | 3 | 3.89 |
| " | 4 | 3.79 |
| " | 5 | 3.42 |
| | mean ± SD | 3.54 ± 0.28 |
| | % RSD | 7.91 |
| | % target * | 80.1 |
| Custom diluent/10 mg Platinol ® | 1 | 3.97 |
| " | 2 | 3.97 |
| " | 3 | 3.88 |
| | Mean ± SD | 3.94 ± 0.05 |
| | % RSD | 1.27 |
| | % target * | 89.1 |
| CD/10 mg Faulding | 1 | 3.73 |
| " | 2 | 3.61 |
| " | 3 | 3.96 |
| " | 4 | 3.78 |
| " | 5 | 3.72 |
| | mean ± SD | 3.76 ± 0.13 |
| | % RSD | 3.46 |
| | % target ** | 93.7 |
| CD/25 mg Faulding | 1 | 3.95 |
| " | 2 | 3.82 |
| " | 3 | 3.82 |

TABLE 2-continued

| Formulation | Sample (Syringe) # | CDDP Content (mg/ml) |
|---|---|---|
| " | 4 | 3.85 |
| " | 5 | 3.73 |
| | mean ± SD | 3.83 ± 0.08 |
| | % RSD | 2.09 |
| | % of target ** | 95.5 |

* 4.4 mg/ml CDDP
** 4.0 mg/ml CDDP

CDDP contents within various portions of syringes containing final gel prepared using either epinephrine containing diluent or WFI are described in Table 3. Gels prepared using custom diluent were found to be equivalent to the gel prepared using WFI as diluent for the lyophilized CDDP, demonstrating that there is no adverse effect on homogeneity of gels in syringes.

TABLE 3

Intrasyringe CDDP Homogeneity in CDDP Gel Implants Prepared with WFI or Custom Diluent

| | Intrasyringe CDDP Content | | |
|---|---|---|---|
| Diluent | mean ± s.d. (mg/ml) | RSD | % of Nominal |
| WFI | 3.62 ± 0.006 | 1.66% | 90.5 |
| WFI | 3.48 ± 0.11 | 3.16% | 87.0 |
| WFI | 3.37 ± 0.14 | 4.15% | 84.3 |
| WFI | 3.43 ± 0.05 | 1.38% | 85.5 |
| custom | 4.17 ± 0.15 | 3.59% | 104.2 |
| custom | 4.02 ± 0.29 | 7.21% | 100.5 |
| custom | 4.02 ± 0.04 | 0.99% | 100.5 |
| custom | 3.97 ± 0.05 | 1.20% | 99.3 |
| custom | 3.97 ± 0.01 | 0.25% | 99.3 |

Example II

Retention of CDDP in RIF-1 Fibrosarcomas in Mice Following Intratumoral Administration of CDDP/Epinephrine Gels This study investigated the effects of different diluents employed in preparation of CDDP/epinephrine injectable gels on tumor drug retention. Diluents included Water for Injection (WFI) or a custom diluent containing 0.1% polysorbate 80. The concentration of the collagen gel in the finished gel preparations was 2%. Test formulations were administered intratumorally, in a single dose, to C3H inbred female mice with RIF-1 syngeneic tumors grown dermally in the flank. Intratumoral injection volume was 20 µl. Eighteen animals were assigned to each treatment group (3 animals per time point and a total of 6 time points, i.e. 0.5, 1, 1.5, 2, 6, and 24 h). After excision, tumor samples were assayed for platinum content via atomic absorption spectroscopy. Platinum retention in tumor was expressed as weight of platinum per weight tumor (in µg/g), and also as percent (%) of the total administered dose. Area under the curve (AUC 0.5 to 24 hour) for local retention in the tumor was calculated by the trapezoidal rule and expressed in µg/g hr (shown in Table 4).

Retention of platinum in tumors was better with the final injectable gels prepared with the polysorbate-containing diluent (288 µg/g hr) than with the gel prepared with WFI (195 µg h/g).

TABLE 4

Time Integrated Intratumoral Platinum Concentration in Mice with RIF-1 Tumors Following Intralesional Administration of CDDP Gel Prepared Using CDDP Suspensions in WFI or Custom Diluent

| diluent | $AUC_{0.5\ to\ 24\ hrs}$ (µg/g hr) |
|---|---|
| WFI | 195 ± 35 |
| custom | 288 ± 46 |

Example III

Effect of Diluent on Efficacy of CDDP/Epinephrine Gels on RIF-1 Tumor Growth in C3H Mice

The effect of variations in diluents employed in the preparation of CDDP/epinephrine injectable gel formulations on antitumor efficacy was determined. Diluents included Water for Injection (WFI) alone and special diluent containing polysorbate 80 as a suspension aid. The two resulting test formulations were administered intratumorally, in a single dose, to normal C3H/Sed inbred female mice with RIF-1 syngeneic tumors grown dermally in the flank. Intratumoral injection volume was 25 or 50 µl. An untreated, contralateral tumor served as an internal control in each animal. The gel formulations contained CDDP at 4 mg/ml and epinephrine at 0.1 or 0.04 mg/ml. Ten animals were assigned to each treatment group. Other control groups (five animals, or ten tumors, per group) included a positive control (i.e. i.p. injection of CDDP solution at the same total drug dose, i.e. 200 µg per animal) and an untreated group of animals. Tumor sizes were measured three times per week for up to one month. Tumor growth delay, defined as the time required for tumors to grow to four times their volume at start of treatment, was used as the assay endpoint.

The two gel formulations examined in several independent studies did not differ appreciably from each other in in vivo tumor efficacy. Tumor growth delay results are shown in Table 5. Tumor growth in untreated control animals occurred fairly rapidly, as expected, with the 4× endpoint reached at an average of 6.4 days. Administration of CDDP intratumorally via the injectable gel system provided a delay of tumor growth, extending the endpoint from 9.4 to over 27.4 days. Tumor growth on the untreated side in these groups was also slightly delayed (6.6–13.7 days) suggesting some systemic availability of the CDDP.

TABLE 5

Effect of Diluent on CDDP/ Epinephrine Gel Efficacy (Gels Prepared Using Either WFI or Custom Diluent; Efficacy Measured via RIF-1 Tumor Growth Delay in Mice)

| | Inj. | | | 4× Tumor Growth | |
|---|---|---|---|---|---|
| Tumor | CDDP conc. (mg/ml) | Vol. (µl) | CDDP Diluent | treated side | untreated side |
| RIF-1 | 4.0/0.1 | 50 | WFI | >27.1 ± 1.6 | 13.7 ± 2.2 |
| | | | custom A | 23.4 ± 1.4 | 12.5 ± 1.2 |
| | | | custom B | >26.7 ± 1.5 | 12.0 ± 1.0 |
| SCCVII | 4.0/0.1 | 50 | WFI | 12.4 | 10.1 |
| | | | custom A | 15.1 | 10.8 |
| SCCVII | 4.0/0.1 | 25 | WFI | 12.7 | 7.4 |
| | | | custom A | 13.2 | 7.6 |
| SCCVII | 4.0/0.1 | 25 | WFI | 11.4 | 7.1 |
| | | | custom A | 9.4 | 6.6 |

Example IV

In Vitro Stability

Short term stability of epinephrine was examined as a function of diluent composition. Vials of diluent prepared as in Example I were subjected to accelerated stability testing by storage at 60° C. Vials of a commercially available injectable epinephrine solution (Adrenalin Chloride Solution, Parke Davis) were similarly treated, as a control. After 7 days and 15 days, samples were analyzed for epinephrine content. The results are shown in Table 6. Epinephrine was shown to be more stable in the special diluent than in the commercial product.

TABLE 6

Stability of Epinephrine

| | % remaining activity (60° C.) | |
|---|---|---|
| Formulation | 7 Days | 15 Days |
| custom diluent | 91.9% | 88.7% |
| Adrenalin ® Chloride | 82.4% | 74.9% |

It is evident from the above results that the subject invention provides for an improved CDDP suspension leading to an improved cisplatin-containing injectable gel. CDDP suspensions acceptable for parenteral use prepared using custom diluent exhibited better dose withdrawal and dose reproducibility than suspensions prepared using water for injection. Cisplatin-containing gels prepared from such suspensions exhibited higher CDDP concentrations and less syringe-to-syringe variability. In all aspects of tested performance, gels made with custom diluent were equivalent to or better than gels made with water for injection.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A stable, aqueous dispersion of cisplatin useful for delivery of cisplatin to a neoplastic lesion in a patient, comprising:

about 0.05 to 0.75% nonionic surfactant, about 2 to 8 mg/ml cisplatin;

about 0.5 to 8% collagen; and about 0.01 to 0.5 mg/ml epinephrine, in an aqueous vehicle.

2. A formulation according to claim 1, further comprising: about 0.01% to 0.25% carboxymethylcellulose sodium.

3. A formulation according to claim 1, wherein said nonionic surfactant is a polysorbate.

4. A formulation according to claim 3, wherein said polysorbate is polysorbate 80.

5. A formulation according to claim 1, comprising from about 0.02 to 0.2 mg/ml epinephrine.

6. A formulation useful for delivery of cisplatin to a neoplastic lesion in a patient, comprising:

about 0.05 to 0.75% polysorbate 80;

about 0.05 to 0.2 mg/ml epinephrine;

about 1.5 to 6.5 mg/ml cisplatin; and about 0.5 to 8% collagen;

in an aqueous vehicle.

7. A formulation according to claim 6, further comprising: about 0.01% to 0.25% carboxymethylcellulose sodium.

8. A method for preparation of a cisplatin dispersion for treatment of a neoplastic lesion in a patient, the method comprising:

resuspending lyophilized cisplatin to form a dispersion of from about 2 to 8 mg/ml cisplatin in an aqueous diluent comprising:

about 0.05 to 0.75% nonionic surfactant and from about 0.01 to 0.5 mg/ml epinephrine.

9. A method according to claim 8, further comprising the step of:

mixing said suspension with a collagen gel to result in an aqueous gel containing about 0.5 to 8.0% collagen.

10. A method according to claim 8, wherein said nonionic surfactant is a polysorbate.

11. A method according to claim 10, wherein said polysorbate is polysorbate 80.

12. A method according to claim 8, wherein said diluent comprises from about 0.02 to 0.2 mg/ml epinephrine.

13. A kit for preparation of a therapeutic cisplatin suspension, comprising:

lyophilized cisplatin; and an aqueous diluent for resuspension of said cisplatin comprising about 0.05 to 0.75% polysorbate 80 and about 0.01 to 0.5 mg/ml epinephrine.

14. A kit according to claim 13, further comprising:

collagen gel.

15. A kit according to claim 13, where said diluent comprises from about 0.02 to 0.2 mg/ml epinephrine.

* * * * *

UNITED STATES PATENT AND TRADEMARK OFFICE
CERTIFICATE OF CORRECTION

PATENT NO.    : 6,224,883 B1
DATED         : May 1, 2001
INVENTOR(S)   : Kathleen V. Roskos et al.

It is certified that error appears in the above-identified patent and that said Letters Patent is hereby corrected as shown below:

<u>Column 7,</u>
After "TABLE 2", insert the title -- Effect of Reconstitution Diluent on Mixing Accuracy --.

Signed and Sealed this

Twentieth Day of August, 2002

*Attest:*

*Attesting Officer*

JAMES E. ROGAN
*Director of the United States Patent and Trademark Office*